United States Patent

Richardson et al.

[11] Patent Number: 5,622,185
[45] Date of Patent: Apr. 22, 1997

[54] BARRIER DEVICE

[75] Inventors: Margaret P. Richardson; Philip Richardson, both of Carmarthen, United Kingdom

[73] Assignee: Chartex International plc, United Kingdom

[21] Appl. No.: 376,460

[22] Filed: Jan. 23, 1995

Related U.S. Application Data

[63] Continuation of Ser. No. 25,388, Mar. 2, 1993, abandoned, which is a continuation of Ser. No. 640,371, filed as PCT/GB89/00726, Jun. 29, 1989, Pat. No. 5,193,555.

[30] Foreign Application Priority Data

Jun. 29, 1988 [GB] United Kingdom ............ 8815457
Jun. 29, 1988 [GB] United Kingdom ............ 8815460
Nov. 21, 1988 [GB] United Kingdom ............ 8827080

[51] Int. Cl.⁶ .................................................. A61F 6/06
[52] U.S. Cl. ........................... 128/842; 128/844; 128/918
[58] Field of Search ........................... 128/830, 832, 128/840, 844, 842, 917, 918

[56] References Cited

U.S. PATENT DOCUMENTS

| | | | |
|---|---|---|---|
| 2,577,345 | 12/1951 | McEwen | 128/844 |
| 3,085,570 | 4/1963 | Penska | 128/844 |
| 4,821,742 | 4/1989 | Phelps, III | 128/842 |
| 4,867,176 | 9/1989 | Lash | 128/844 X |
| 4,945,923 | 8/1990 | Evans et al. | 128/842 |
| 4,972,849 | 11/1990 | Park et al. | 128/844 X |

*Primary Examiner*—Sam Rimell
*Attorney, Agent, or Firm*—Banner & Allegretti, Ltd.

[57] ABSTRACT

The device, for use in contraception and in preventing transmission of sexually transmitted diseases, comprises a thin, flexible pouch having an open end in the form of a peripheral flange with a peripheral ribbed rim, and a closed end. An insert is provided within the closed end of the pouch so as to protect the pouch during insertion thereof into the vagina by means of an applicator rod or the like. The insert, which is typically absorbent and of flexible expanded plastics material, and may have dispersed therein a spermicide and/or an antiviral agent, comprises a central portion and four spurs. A continuous coating layer of an adhesive material which can temporarily adhere the barrier device to mucous membrane material in the presence of aqueous body fluids is preferably provided on the vulva-contacting surface of the flange and/or on the vagina-contacting surface of the pouch.

7 Claims, 1 Drawing Sheet

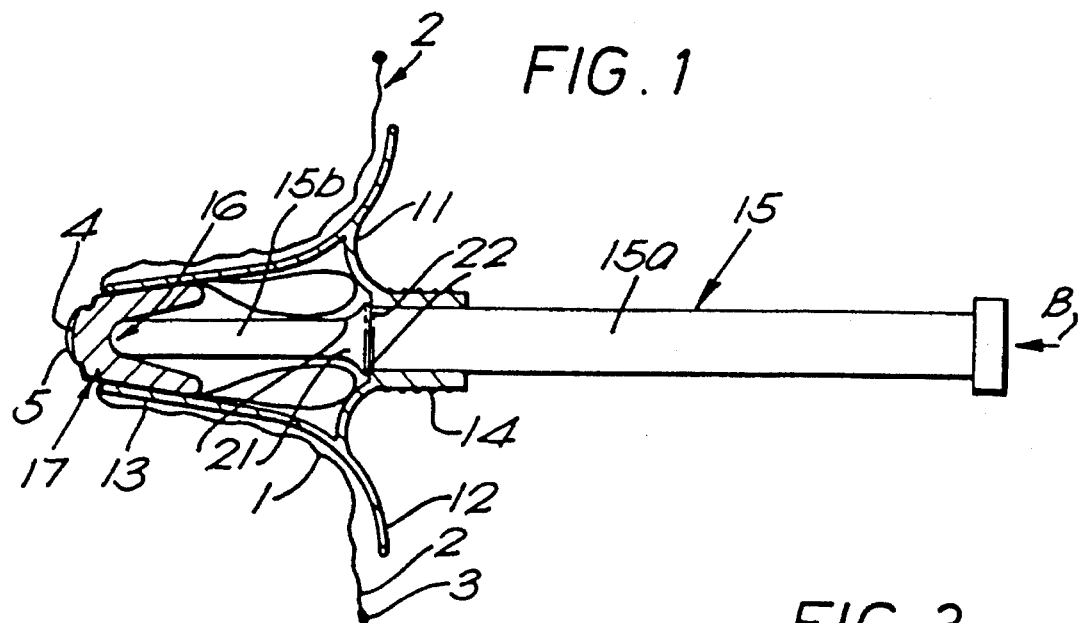
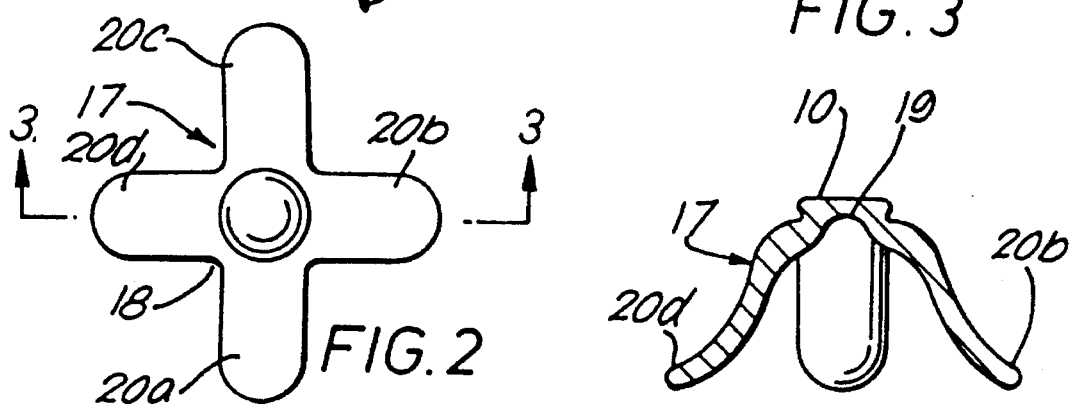
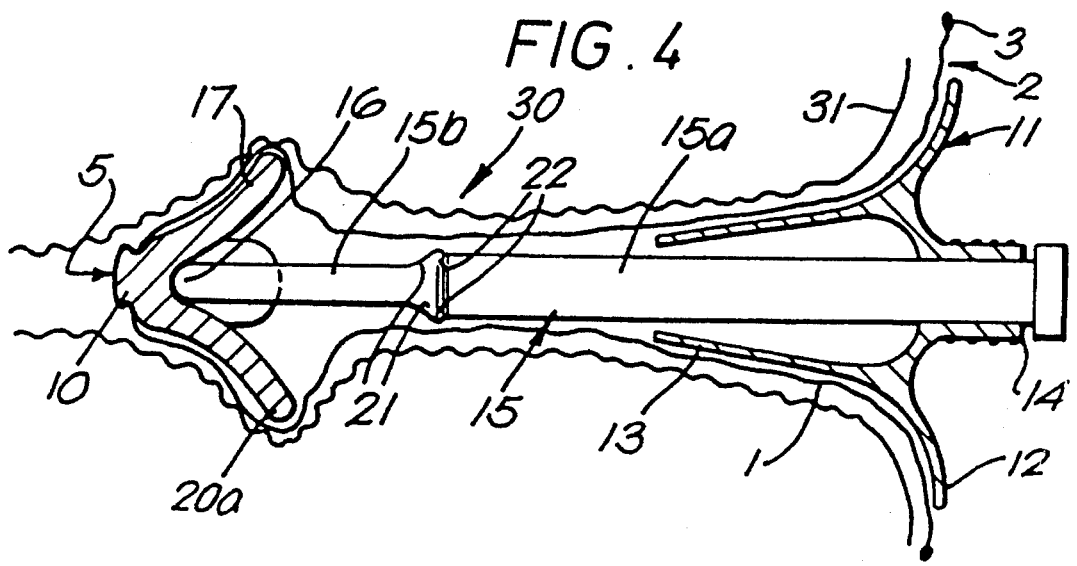

BARRIER DEVICE

This application is a continuation of application Ser. No. 08/025,388 filed on Mar. 2, 1993, abandoned which was a continuation of application Ser. No. 07/640,371, filed as PCT/GB89/00726, Jun. 29, 1989 now U.S. Pat. No. 5,193,555.

The present invention is concerned with barrier devices for use in contraception and in preventing transmission of sexually transmitted diseases.

It is known that barrier-type contraceptive devices ("condoms") are effective not only as contraceptives, but also to help prevent sexual transmission of diseases. Indeed the use of a condom Is positively recommended as a prophylactic measure against, in particular, acquired immune deficiency syndrome (AIDS).

Condoms have, traditionally, been only suitable for use by the male partner; they can only be donned on an erect penis, immediately before intercourse. This has been found to be off-putting by many users and the resulting delay can sometimes lead to loss of erection by the male; furthermore, the traditional male condom permits contact between vaginal mucous membranes and the penis at the entrance to the vagina, with consequent risk of disease transmission. The male condom may become dislodged under certain circumstances during intercourse (e.g. on loss of erection or withdrawal of the penis), with consequent failure of the contraceptive and disease-preventing barrier.

In order to alleviate these disadvantages and provide an alternative means of contraception and prevention of sexual transmission of diseases, the so-called "female condom" has been developed. One such "female condom" (as described in our PCI Patent Application GB88/00042) is a barrier device which comprises a continuous, liquid-impermeable shield member shaped and dimensioned so that, in its operational position, it covers the entrance of a user's vagina, the shield member having integral therewith a continuous liquid-impermeable flexible pouch arranged to be introduced into the vagina so as to form a liquid barrier between the penis and the vagina; and means for securing the shield member in the operational position.

We have now devised an improvement in such barrier devices, which can be suitable for use either as female condoms or as male condoms.

According to a first aspect of the present invention, therefore, there is provided a barrier device comprising a continuous, liquid-impermeable, flexible pouch having an open end and a closed end such that the pouch can form a liquid barrier between a penis and a vagina; and a soft resilient insert arranged for insertion in said pouch between the tip of the penis and said closed end, said insert comprising a generally central portion and, extending outwardly from said central portion, means for biasing said pouch in the vicinity of said closed end into contact with the walls of the vagina.

According to a second aspect of the present invention, there is provided a barrier device comprising a continuous, liquid-impermeable, flexible pouch having an open end and a closed end such that the pouch can form a liquid barrier between a penis and a vagina; and a soft absorbent resilient insert arranged for insertion in said pouch between the tip of the penis and said closed end, said insert being arranged for biasing said pouch in the vicinity of said closed end into contact with the walls of the vagina.

The resilient insert is such that it facilitates insertion of the pouch into the vagina, either by means of a separate applicator body, by the use of a finger or by means of the penis. Alternatively, when the pouch is donned by the male prior to coitus, with the insert located at the tip of the penis, the insert serves to maintain the pouch in position during intercourse, and, in some embodiments, after withdrawal of the penis. In addition to fulfilling these functions, the insert enhances tactile pleasure for the users and (when of absorbent material) may assist in absorption of sperm.

The resilient insert is typically of flexible expanded polymeric material, sponge rubber, solid rubber, plastics or the like; in some embodiments it is, as indicated above, absorbent. The insert typically comprises a central body portion and a plurality of radially outwardly projecting spurs (such as three or four such spurs). In some embodiments, the body portion has a central depression for receiving the tip of an applicator rod or the like, and three, four or more outwardly projecting spurs. The body portion may further comprise a formation on its face remote from the latter depression which is arranged to engage with a complementary formation (typically in the form of a teat or the like) provided on the internal surface (that is, the penis-contacting surface) of the pouch, such that the insert is retained in position when the pouch is inserted in the vagina. Typically, the formation on the body portion comprises a protrusion and the complementary formation on the internal surface of the pouch comprises a depression capable of receiving the protrusion. Alternatively, the resilient insert may be retained in position by an adhesive coating on the insert and/or on the internal surface of the pouch.

It is preferred in some embodiments of the invention that the insert should contain a spermicide and/or a fungicide, bactericide or anti-vital agent, which is such that it is slowly released in situ. Certain embodiments of the barrier device according to the invention are suitable for use as male condoms; further embodiments are suitable for use as female condoms; and still further embodiments are suitable for use as either, according to choice.

When the device is intended for use as a female condom, the open end of the pouch preferably has, integral therewith, a continuous liquid-impermeable peripheral flange arranged to cover the vulva (around the periphery of vaginal entrance). In this case, the barrier device may be employed together with an elongate applicator body (in the form of a rod or the like) which is arranged to introduce the pouch into the vagina and be withdrawn therefrom, so as to leave the pouch in place. When the applicator body is thus withdrawn, the biasing means acts to retain the pouch in place in the vagina.

It is preferred that such a peripheral flange should have bonded thereto on the vulva-contacting surface and/or on the vagina contacting surface a continuous coating layer of an adhesive material which is such that it can temporarily adhere the surface to mucous membrane material in the presence of aqueous body fluids.

The use of such a coating layer is believed to be novel per se; the present invention therefore further comprises a barrier device comprising a continuous liquid-impermeable shield member shaped and dimensioned so that, in its operational position, it substantially covers a user's vulva, the shield member having integral therewith a continuous liquid-impermeable flexible pouch arranged to be introduced into the user's vagina so as to form a liquid barrier during coitus between the vagina and the penis; and means for securing the shield member in the operational position, in which the vulva-contacting surface of the shield member and/or the vagina-contacting surface of the pouch has bonded thereto a substantially continuous coating layer of an adhesive material which is such that it can temporarily adhere said barrier device to mucous membrane material in the presence of aqueous body fluids.

An example of a preferred adhesive material is a hydrogel-type material, which is preferably a hydrophilic synthetic polymer. Examples of suitable such polymers are polymers of vinyl pyrrolidone, hydroxyalkyl acrylates or methacrylates, of an acrylamide; such polymers generally have (in addition to temporary adhesive properties for holding the device in place in the vagina), lubricating properties.

Such an adhesive coating layer or layers preferably contains, in addition to a hydrophilic polymer vehicle, a physiologically acceptable fungicide and/or bactericide, and, most preferably, a spermicide. It is particularly preferred to incorporate a spermicide, such as an ethoxylated alcohol (for example, the material commercially available under the trade mark "Nonoxinol" which is also believed to have anti-viral properties) in the coating layer.

In a further preferred embodiment of the invention, the internal surface (that is, the penis-contacting surface) of the device according to the invention is itself provided with a preformed coating layer having lubricating properties; an example of a suitable type of coating layer is a layer comprising a hydrogel polymer as described above.

The sheath may be of any suitable rubber or plastics material; by way of example, the sheath may be of dipped rubber (of, for example, natural rubber), polyurethane or the like. It is preferred that the sheath and the shield member should together constitute a seamless unitary body.

The present invention further comprises a modification of the female condom device Just described, which comprises a device for use by either a male or female user in which the pouch is arranged to be introduced into the anal passage of the user. In this modification of the invention, the peripheral flange is arranged to cover the periphery of the anal passage, and all references herein to "vagina" and "vaginal walls" are, when relevant to this embodiment, to be construed as respectively reference to the anal passage and the walls thereof.

A preferred embodiment of the present invention will now be described with reference to the accompanying drawings, in which:

FIG. 1 is a longitudinal sectional view of an exemplary barrier device according to the invention, together with an applicator therefor;

FIG. 2 is a plan view of an insert for a barrier device such as that shown in FIG. 1;

FIG. 3 is a sectional view along line A—A in FIG. 2; and

FIG. 4 is a longitudinal section of the device of FIG. 1 when in the process of being inserted into the user's vagina by means of an applicator.

Referring to FIG. 1, there is shown a barrier device in the form of a thin, flexible pouch 1 having an open end 2 in the form of a peripheral flange with a peripheral ribbed rim 3, and a closed end 4, the portion of the pouch between the open and closed ends being folded in upon itself within an applicator body 11. The closed end 4 has a teat-like projection 5 (with a corresponding recess in the internal surface thereof).

The applicator body 11 is in the form of an inwardly tapering tube, tapering from a flanged end 12 to a narrowed end 13; integral with the flanged end 12 is a further tapering tubular portion 14, tapering inwardly in the direction leading away from narrowed end 13. Tapering portion 14 terminates with 8 generally cylindrical portion, which engages with the external surface of an applicator rod 15 having a gripping portion 15a and a portion 15b which is to be inserted into the applicator body; the latter portion is of reduced diameter relative to the gripping portion and connected thereto by a tapered shoulder 21. The connection 22 between the shoulder 21 and portion 15b is of slightly increased diameter, so as to inhibit inadvertent withdrawal of the applicator rod from the applicator body. The tip 16 of the end portion 15b (which is typically part-spherical) engages with insert 17 within the closed end 4 of barrier device; the insert acts to protect the material of the pouch during insertion thereof into the vagina by means of the applicator cod 15.

Referring to FIGS. 2 and 3, the insert 17, which is typically of flexible expanded plastics material having dispersed therein a spermicide and/or an antiviral agent, comprises a central portion 18 having a generally part-spherical recess 19 (shaped to receive the tip 16 of applicator rod 15), and (extending radially outwardly from central portion 18) four spurs 20a, 20b, 20c, 20d. The obverse of central portion 18 has a button-like projection 10 capable of engaging the recess in the internal surface of the closed end 4 of pouch 1 (see FIG. 4).

In operation, as illustrated in FIG. 4, the pouch 1 and the applicator body 11 are together inserted into the user's vagina in the orientation shown in FIG. 1; applicator cod 15 is then pushed manually in the direction of arrow B so as to extend the pouch to its fullest extent within the vagina, to the orientation shown in FIG. 4. The projection 10 engages the closed end of the pouch 1 so that the insect 17 is correctly located. When the cod has been fully inserted, the spurs 20a, 20b, 20c, 20d open out to cause the closed end 4 of the pouch to engage with the vaginal walls 30; the applicator cod 15 and the applicator body 11 are then withdrawn, leaving the pouch in place with the open end 2 in contact with the vulva 31.

The open end 2 of the pouch may be provided with an adhesive coating of the type described above on the vulva-contacting surface.

We claim:

1. A barrier device comprising:

a continuous, liquid-impermeable, flexible pouch having an open end, a closed end, and a diameter, said diameter being sufficiently large to permit movement of a penis within said pouch, said pouch forms a liquid barrier membrane having a penis-contacting surface and a vagina-contacting surface; and a soft resilient insert for insertion in said pouch between the tip of said penis and said closed end, said insert includes:

a generally central portion-forming spacing member between said tip of said penis and said closed end and radially spaced from said central portion;

means for biasing said pouch in a vicinity of said closed end into contact with the walls of the vagina; and a central depression in said soft resilient insert, said central depression receives said tip of said penis, wherein said soft resilient insert includes a central body portion and a plurality of radially outwardly projectiong spurs.

2. The barrier device according to claim 1, wherein there are up to four of said spurs.

3. The barrier device according to claim 2, wherein said central depression in said soft resilient insert receives an applicator.

4. The barrier device according to claim 3, wherein said soft resilient insert further includes a formation on a face remote from said central depression, said formation being arranged to engage with a complementary formation provided on said penis-contacting surface of said pouch whereby said soft resilient insert is retained in position in said vagina.

5. The barrier device according to claim 4, wherein said formation on said soft resilient insert includes a protrusion and said complementary formation on said penis-contacting surface of said pouch includes a depression for receiving said protrusion.

6. A barrier device comprising:

a continuous, liquid-impermeable, flexible pouch having an open end, a closed end, and a diameter, said diameter being sufficiently large to permit movement of a penis within said pouch, said pouch forms a liquid barrier membrane having a penis-contacting surface and a vagina-contacting surface; and a soft resilient insert for insertion in said pouch between the tip of said penis and said closed end, said insert includes:

a generally central portion-forming spacing member between said tip of said penis and said closed end and radially spaced from said central portion;

means for biasing said pouch in a vicinity of said closed end into contact with the walls of the vagina; and a central depression in said soft resilient insert, said central depression receives said tip of said penis, wherein an adhesive coating is provided on said penis-contacting surface of said pouch.

7. A barrier device comprising:

a continuous, liquid-impermeable, flexible pouch having an open end, a closed end, and a diameter, said diameter being sufficiently large to permit movement of a penis within said pouch, said pouch forms a liquid barrier membrane having a penis-contacting surface and a vagina-contacting surface; and a soft resilient insert for insertion in said pouch between the tip of said penis and said closed end, said insert includes:

a generally central portion-forming spacing member between said tip of said penis and said closed end and radially spaced from said central portion;

means for biasing said pouch in a vicinity of said closed end into contact with the walls of the vagina; and a central depression in said soft resilient insert, said central depression receives said tip of said penis, wherein said oen end of said pouch has, integral therewith, a continuous liquid-impermeable peripheral shield member to cover the vulva.

* * * * *